(12) United States Patent
Cao et al.

(10) Patent No.: US 11,447,529 B2
(45) Date of Patent: Sep. 20, 2022

(54) MICROCIN MCCY, AND PREPARATION METHOD AND USE THEREOF

(71) Applicant: South China Agricultural University, Guangzhou (CN)

(72) Inventors: Weisheng Cao, Guangzhou (CN); Yu Li, Guangzhou (CN); Saixiang Feng, Guangzhou (CN)

(73) Assignee: South China Agricultural University, Guangzhou (CN)

( * ) Notice: Subject to any disclaimer, the term of this patent is extended or adjusted under 35 U.S.C. 154(b) by 0 days.

(21) Appl. No.: 17/238,749

(22) Filed: Apr. 23, 2021

(65) Prior Publication Data

US 2022/0235098 A1 Jul. 28, 2022

(30) Foreign Application Priority Data

Jan. 22, 2021 (CN) .......................... 202110087972.9

(51) Int. Cl.
*C07K 14/24* (2006.01)
*C12P 21/02* (2006.01)

(52) U.S. Cl.
CPC .............. *C07K 14/24* (2013.01); *C12P 21/02* (2013.01)

(58) Field of Classification Search
None
See application file for complete search history.

(56) References Cited

PUBLICATIONS https://www.fda.gov/food/laboratory-methods-food/barn-media-m20-blood-agar (accessed Mar. 3, 2022).*

Adamberg et al (Frontiers in Nutrition, 1:1-10, 2014).*
First Office Action issued by the The State Intellectual Property Office of People's Republic China for corresponding Chinese Patent Application No. 202110087972.9, dated Aug. 10, 2021, with an English translation.
Notification to Grant Patent Right for Invention issued by The State Intellectual Property Office of People's Republic China for corresponding Chinese Patent Application No. 202110087972.9, dated Sep. 6, 2021, with an English translation.
Ashton et al., GenBank: EAB7495030.1, "acinetodin/klebsidin/J25 family lasso peptide [*Salmonella enterica* subsp. *enterica*]", Feb. 20, 2019.

* cited by examiner

*Primary Examiner* — Brian Gangle
(74) *Attorney, Agent, or Firm* — Myers Wolin, LLC

(57) ABSTRACT

The present disclosure discloses a Microcin MccY, and a preparation method and use thereof, wherein the amino acid sequence of the Microcin MccY is GGRGHIAEYFSG-PITQVSFYG. Compared with Microcin MccJ25 that only has a bactericidal activity against a small part of serotypes of *Salmonella* such as *Salmonella enteritidis*, the Microcin MccY has bacteriostatic/bactericidal effects on *Salmonella Pullorum, Salmonella typhimurium, Salmonella kentucky, Salmonella Infantis, Salmonella* London, and *Shigella sonnei*, and can kill other serotypes of *Salmonella* that MccJ25 cannot kill. Especially, the Microcin MccY has an outstanding bactericidal effect on *Salmonella typhimurium* and *Salmonella Pullorum* which are common in livestock and poultry production, and meanwhile it also has bacteriostatic/bactericidal effects on *Shigella sonnei*. Therefore, the Microcin MccY overcomes the shortcoming of the narrow spectrum of the Microcin, has breakthrough significance, and has the potential as a substitute to antibiotics.

7 Claims, 5 Drawing Sheets

Specification includes a Sequence Listing.

SEQUENCE LISTING

```
<160> NUMBER OF SEQ ID NOS: 10

<210> SEQ ID NO 1
<211> LENGTH: 21
<212> TYPE: PRT
<213> ORGANISM: Artificial sequence
<220> FEATURE:
<223> OTHER INFORMATION: Primer

<400> SEQUENCE: 1

Gly Gly Arg Gly His Ile Ala Glu Tyr Phe Ser Gly Pro Ile Thr Gln
1               5                   10                  15

Val Ser Phe Tyr Gly
            20

<210> SEQ ID NO 2
<211> LENGTH: 162
<212> TYPE: DNA
<213> ORGANISM: Artificial sequence
<220> FEATURE:
<223> OTHER INFORMATION: Primer

<400> SEQUENCE: 2
atgttcaaga aactctttag ttcgagtaaa gggcacgctg tgaaaaaaat tccaggggta      60
gttcggattc aaacgccagc ttcacaactc acaaaaggtg gtcgggggca tatcgcggaa     120
tatttttccg gtccgatcac ccaagtatcg ttctacggtt aa                        162

<210> SEQ ID NO 3
<211> LENGTH: 633
<212> TYPE: DNA
<213> ORGANISM: Artificial sequence
<220> FEATURE:
<223> OTHER INFORMATION: Primer

<400> SEQUENCE: 3
atgactcgtt atggcttcac ccggtacaaa accgatctag tgatacttga tgctgttaaa      60
gatgaattct acctgctgcc tggcgcaggt cagtttctgg aagacagggc tgaattgctc     120
```

```
aagcggtacc cacaactgtg tgagtatctg atagtgagc attatatcgg aagtacagcg      180
gagaataaaa acctctcttt tctcgaagaa cgttggttga tgcctgaacc tgtaaacgta      240
tcaaccctcc cctccttttt tcagcgaatg atgctactgg caaaaatact gtattacagt      300
aaaagcatag aaaaaagggg gatgggatgg atttataata aaaacaaaag agacgcaaaa      360
cctgccgcta tgtctgcaaa tcaggagatt ataattcagg agacggtaag tacagtttca      420
tcacttttct gtattaatat gttcaaatca gattgcctga catactcatt cactttaaaa      480
aatgcactat attcccgagg agttgatgcc agactggtaa ttggagtccg gactcaacca      540
ttttacagtc atgcatgggt tgagatcgaa ggtaacatca tcaatgatga ccctgacctg      600
agagataagt tgtctgtcat tgcagagata taa                                   633
```

<210> SEQ ID NO 4
<211> LENGTH: 1533
<212> TYPE: DNA
<213> ORGANISM: Artificial sequence
<220> FEATURE:
<223> OTHER INFORMATION: Primer

<400> SEQUENCE: 4

```
atgagaaatt ccttcataca gtttaaagaa aaaaaaatca cactgaactt ttgtgatgcg       60
ttaacagtgt ttcggaatga tcatgttaca gttatgctta aaggtaaggc atatttaaaa      120
aacaaaggcc taacagttga aggtatagcc agagaagttg tttcaagagg cgtatataac      180
gtaattaatg aattaactgg catttctgt gcttttatat tccatgaaaa ttatatctat       240
atgggcagga gcatgcattc cggccctcag ttgttttatc atattaatgg ggatgcgcta      300
tacatcgcag ataaaataag tgaattaatt aaattacctg gttttacagg cagcctaaat      360
ttgcgtgtgg cgcagaaata tcttaatgga tgccgtaata atgacaatga ttcttttatt      420
accggagttc ataaaattaa caacggtgaa tttgtaaaat ttgattatca actttcctct      480
acttctgtca tcgatgagtt ctgtattaag aaaaaaaacg actctgtcat tgataatgtc      540
atatctaata tcgaaatgac acatgaaaac agagatataa cattgctttt ctcaggaggg      600
tttgattcct cactggtttt tcatgccctc aaagaattgg gatttatgtt cagatcttgt      660
tattatgttt ctgagtattc tgatgacagc gaaatggaat ttgcccgtag gtattgctta      720
aagtatggcg tggaattcgc ggctataaat aaaaaaattg atttcaatga agagcattat      780
tatgaattaa atcctgacgt cccggatgag atcccattag ctcctgagtt atcatgtgag      840
tcagaggaat cttatgggtt gaagagtgaa atggtttttt taatctgtgg tcatggcggg      900
gatcatattt ttggtcagaa tccatctgta ctgtttgggc ttgatgccct tcgtaagcat      960
ggtataaaaa ccatgcataa aaaaatggtt gaatattcct gccttaaggg attgaagtac     1020
aaggatattt ttattaaaaa catggctgcg ttaagacaaa aaccggcaat gtatacactg     1080
gcaaaagatg aacacatctc tactatgagg ctggcatccg ctcagttctt ttctgttgat     1140
atacgcaata agtaaacat attcacacca ttcttattta aaaatattgt acagcaccat     1200
gtttcactgc ctgtttatga gttatttaac caacaatatg accggtatcc catgcgattt     1260
gaggcattca gtcgttacgg gtcagatatc ttctggaaga aatcaaagag gtcttcttca     1320
cagcttattt tcagaatcct ttctgaaaaa tgtgaaaata tagccaatgc gattgaacaa     1380
```

```
tctggccttg ctgatgccat gaatattaat cattctgaat taagtaaaga tttgtatgaa      1440
aacactagag ttctattgac agatcgatta ccttatctca ttagtctgta ccaactggca      1500
aaatacatgc agattcacag aatcaatatt tga                                   1533
```

<210> SEQ ID NO 5
<211> LENGTH: 1761
<212> TYPE: DNA
<213> ORGANISM: Artificial sequence
<220> FEATURE:
<223> OTHER INFORMATION: Primer

<400> SEQUENCE: 5

```
atgtcaaatt atatcaagac ttcgcttcca gcttacatat actcactaat ggatagcaaa       60
gggagggttt tattttttcgg catgcttttt gttacatctc tttcatccat tataatatca     120
gtttcacctt tcttgcttgc aaaaattacc gatttattag tgggttacca gtctagccgg     180
ggtagtgatt tcagtattaa ctatcttatt atattatcat gcttgtatat gttctgtgtg     240
atatacaata aaccagttc gtttctattt atggtactcc agagcaatct tcgcataaga     300
atttcgaaaa aatgtccct acgctacctg gaggcacttt ataaggaaga tattaataag     360
cttgataaaa acaatgcagg atttacaaca caacgtctca atcaggcttc taacgacatt     420
tatatccttg taaggaatgt tgctcaaaat atactctcac ctgcaattca acttatatcg     480 gcagttttg ttgtgttatc aactcgtgac tggttctcag ccagtgtatt tttagtatac     540
atcgttattt ttattatatt caatgtgagg ctaactgatt cattagcctc cctgcgtaag     600
aacagtatgg atatcaccct tcagtcatat agtttgttat ctgataccgt tgacaacatg     660
attggggcaa agaaaaataa tgctctcaag caagtttcag atcgttatga acaagctcta     720
acgaccgaaa gtaaagcaca gcaaaaattc tggaattta gtgcctgggt tctcttatta     780
aattccgcac ttgctgttat ttatttggt gcagtttttt cttataatct ttcgggcgtt     840
attaatggaa gtgcatccat tggccatttc atcatgatca cctcctatat tatacttctt     900
tctacgccag tagagaatat aggttctctt ctcagtgaaa tacgacaatc aatattcagt     960
cttgagggtt ttctcgctca tcataaagat gccgataact gttctaatgc taataataat    1020
gttttaacta agtcgaatgg taaaacaaac atatccatca aagaacttc atttggatac    1080 gttacaggga agcagatcct taaaaatata aatataaaac ttacagcagg taaaatatat    1140
tctttgacag gccctagtgg ctcaggaaaa tcaacgcttg ttaagcttat ttcagggtac    1200
tacagtaatt attcgggtgg gatttacctt aatgatgttt cgctgcagga tctctgtgat    1260
gaggaactta acgaaaccat ttatcatctt acccaggatg attatatttt catggatacc    1320
cttcgcttta atcttcgcct ggcccggtac gatgcatcag agaaggagat gcttgatgtg    1380
ctcagtcttg ctaacctatc taagataggt aatgaacccg ttagtctgga tacatctctt    1440
acgagtaaag gtaataacta ttctggaggg cagaaacaaa ggctctctct tgcacgacta    1500 ttttttacgct ctccgtctgt aattatcatc gatgaggcaa catcagctct tgattacatt    1560
aatgaatctg aaataatgac ctcaataaaa aaatattttc ctgatgcgct gataataaat    1620
attagtcacc gcgtaagcct tcttgagtgc tctgactatg tttatgttct cgacgatggg    1680
cagattgtcg cttcaggtca attccatgaa ctgaaggcca gcaactgtta tattaacggc    1740
ctggcatcag ctacagaata a                                              1761
```

<210> SEQ ID NO 6

<211> LENGTH: 4458
<212> TYPE: DNA
<213> ORGANISM: Artificial sequence
<220> FEATURE:
<223> OTHER INFORMATION: Primer

<400> SEQUENCE: 6

| | |
|---|---|
| ataaaagctg acttgtgtga tagggccact aaaatactcc gcaatgtgac cacgtcctcc | 60 |
| tttagttaat tgtgaggctg gtgtctgaat tctaacaaca cctggaattt tttttactgc | 120 |
| atgaccttta gagctggaaa ataatttttt aaacatttat cacttcctct gtagattaaa | 180 |
| cagttttgga aaaaacagaa ccatacatcg gttctgtaag gaaatgtgta acatagaatt | 240 |
| gaaatgctat caagaatcat ttgtgtttgg ataattttgt tacattacag taagttaaga | 300 |
| gttattgttg atattttgca ctatcgattt ggtgaaaaaa gaaacatttg tttgtaagtt | 360 |
| tatgtaatcc gtcatcactg gcagataaat actctgttat agataatata ttttattcga | 420 |
| ggtgagaatt ttatgaacta atcagtatta gttcttttca caggctgagt tatatgacta | 480 |
| agatgcatta agcgtttttt tttgagagca gggagaacat attgactcgt tatggcttca | 540 |
| cccggtacaa aaccgatcta gtgatacttg atgctgttaa agatgaattc tacctgctgc | 600 |
| ctggcgcagg tcagtttctg gaagacaggg ctgaattgct caagcggtac ccacaactgt | 660 |
| gtgagtatct ggatagtgag cattatatcg gaagtacagc ggagaataaa aacctctctt | 720 |
| ttctcgaaga acgttggttg atgcctgaac ctgtaaacgt atcaaccctc ccctcctttt | 780 |
| ttcagcgaat gatgctactg gcaaaaatac tgtattacag taaaagcata gaaaaaaagg | 840 |
| ggatgggatg gatttataat aaaaacaaaa gagacgcaaa acctgccgct atgtctgcaa | 900 |
| atcaggagat tataattcag gagacggtaa gtacagtttc atcactttc tgtattaata | 960 |
| tgttcaaatc agattgcctg acatactcat tcactttaaa aaatgcacta tattcccgag | 1020 |
| gagttgatgc cagactggta attggagtcc ggactcaacc attttacagt catgcatggg | 1080 |
| ttgagatcga aggtaacatc atcaatgatg accctgacct gagagataag ttgtctgtca | 1140 |
| ttgcagagat ataaatatga gaaattcctt catacagttt aaagaaaaaa aaatcacact | 1200 |
| gaacttttgt gatgcgttaa cagtgtttcg gaatgatcat gttacagtta tgcttaaagg | 1260 |
| taaggcatat ttaaaaaaca aaggcctaac agttgaaggt atagccagag aagttgtttc | 1320 |
| aagaggcgta tataacgtaa ttaatgaatt aactggcatt ttctgtgctt ttatattcca | 1380 |
| tgaaaattat atctatatgg gcaggagcat gcattccggc cctcagttgt tttatcatat | 1440 |
| taatggggat gcgctataca tcgcagataa aataagtgaa ttaattaaat tacctggttt | 1500 |
| tacaggcagc ctaaatttgc gtgtggcgca gaaatatctt aatggatgcc gtaataatga | 1560 |
| caatgattct tttattaccg gagttcataa aattaacaac ggtgaatttg taaaatttga | 1620 |
| ttatcaactt tcctctactt ctgtcatcga tgagttctgt attaagaaaa aaacgactc | 1680 |
| tgtcattgat aatgtcatat ctaatatcga aatgacacat gaaaacagag atataacatt | 1740 |
| gcttttctca ggagggtttg attcctcact ggttttcat gccctcaaag aattgggatt | 1800 |
| tatgttcaga tcttgttatt atgtttctga gtattctgat gacagcgaaa tggaatttgc | 1860 |
| ccgtaggtat tgcttaaagt atggcgtgga attcgcggct ataaataaaa aaattgattt | 1920 |
| caatgaagag cattattatg aattaaatcc tgacgtcccg gatgagatcc cattagctcc | 1980 |
| tgagttatca tgtgagtcag aggaatctta tgggttgaag agtgaaaatg gttttttaat | 2040 |
| ctgtggtcat ggcggggatc atattttggg tcagaatcca tctgtactgt ttgggcttga | 2100 |
| tgcccttcgt aagcatggta taaaaaccat gcataaaaaa atggttgaat attcctgcct | 2160 |

```
taagggattg aagtacaagg atatttttat taaaaacatg gctgcgttaa gacaaaaacc    2220
ggcaatgtat acactggcaa aagatgaaca catctctact atgaggctgg catccgctca    2280
gttcttttct gttgatatac gcaataaagt aaacatattc acaccattct tatttaaaaa    2340
tattgtacag caccatgttt cactgcctgt ttatgagtta tttaaccaac aatatgaccg    2400
gtatcccatg cgatttgagg cattcagtcg ttacgggtca gatatcttct ggaagaaatc    2460
aaagaggtct tcttcacagc ttattttcag aatcctttct gaaaaatgtg aaaatatagc    2520
caatgcgatt gaacaatctg gccttgctga tgccatgaat attaatcatt ctgaattaag    2580
taaagatttg tatgaaaaca ctagagttct attgacagat cgattacctt atctcattag    2640
tctgtaccaa ctggcaaaat acatgcagat tcacagaatc aatatttgaa ggtgtttatg    2700
tcaaattata tcaagacttc gcttccagct tacatatact cactaatgga tagcaaaggg    2760
agggttttat ttttcggcat gcttttgtt acatctcttt catccattat aatatcagtt    2820
tcacctttct tgcttgcaaa aattaccgat ttattagtgg gttaccagtc tagccggggt    2880
agtgatttca gtattaacta tcttattata ttatcatgct tgtatatgtt ctgtgtgata    2940
tacaataaaa ccagttcgtt tctatttatg gtactccaga gcaatcttcg cataagaatt    3000
tcgaaaaaaa tgtccctacg ctacctggag gcactttata aggaagatat taataagctt    3060
gataaaaaca atgcaggatt tacaacacaa cgtctcaatc aggcttctaa cgacatttat    3120
atccttgtaa ggaatgttgc tcaaaatata ctctcacctg caattcaact tatatcggca    3180 gttttttgttg tgttatcaac tcgtgactgg ttctcagcca gtgtatttt agtatacatc    3240 gttatttta ttatattcaa tgtgaggcta actgattcat tagcctccct gcgtaagaac    3300
agtatggata tcacccttca gtcatatagt ttgttatctg ataccgttga caacatgatt    3360
ggggcaaaga aaaataatgc tctcaagcaa gtttcagatc gttatgaaca agctctaacg    3420
accgaaagta aagcacagca aaaattctgg aattttagtg cctgggttct cttattaaat    3480
tccgcacttg ctgttatttt atttggtgca gttttttctt ataatctttc gggcgttatt    3540
aatgaaagtg catccattgg ccatttcatc atgatcacct cctatattat acttcttct    3600 acgccagtag agaatatagg ttctcttctc agtgaaatac gacaatcaat attcagtctt    3660
gagggttttc tcgctcatca taaagatgcc gataactgtt ctaatgctaa taataatgtt    3720
ttaactaagt cgaatggtaa aacaaacata tccatcaaag aactttcatt tggatacgtt    3780
acagggaagc agatccttaa aaatataaat ataaaactta cagcaggtaa aatatattct    3840
ttgacaggcc ctagtggctc aggaaaatca acgcttgtta agcttatttc agggtactac    3900
agtaattatt cgggtgggat ttaccttaat gatgtttcgc tgcaggatct ctgtgatgag    3960
gaacttaacg aaaccattta tcatcttacc caggatgatt atattttcat ggataccctt    4020
cgctttaatc ttcgcctggc ccggtacgat gcatcagaga aggagatgct tgatgtgctc    4080
agtcttgcta acctatctaa gataggtaat gaacccgtta gtctggatac atctcttacg    4140
agtaaaggta ataactattc tggagggcag aaacaaaggc tctctcttgc acgactattt    4200
ttacgctctc cgtctgtaat tatcatcgat gaggcaacat cagctcttga ttacattaat    4260
gaatctgaaa taatgacctc aataaaaaaa tatttttcctg atgcgctgat aataaatatt    4320
agtcaccgcg taagccttct tgagtgctct gactatgttt atgttctcga cgatgggcag    4380
attgtcgctt caggtcaatt ccatgaactg aaggccagca actgttatat taacggcctg    4440
gcatcagcta cagaataa                                                  4458
```

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
taatacgact cactataggg                                              20

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8
gctagttatt gctcagcgg                                               19

<210> SEQ ID NO 9
<211> LENGTH: 4495
<212> TYPE: DNA
<213> ORGANISM: Artificial sequence
<220> FEATURE:
<223> OTHER INFORMATION: Primer

<400> SEQUENCE: 9
tcagccatag aaagatatag gtgtaccaat ccccacaaaa tactcaggca catgtcctgc     60
accacctttt gtgagttgcg atgctgattt ttttatttgt ataacccct ttgcaggaga    120 tggaacatta ttttttttac cagaagacag tttattaaaa tgaaaatgct taatcatttt    180
tacgttcctt atttgatgaa aatagtatga tgatttttac agaggaacct cacgtccttc    240
tgttagaatt ttattagcac aaaataaaat tgagatcaat aatcattacg ctttagtaat    300
ttatcaataa aattatttag atacaaacat ccataaacta atcaatctgc aaaagtggtc    360
aaatttagta caatattttg gattttata cattttctta attatttcag aatatttagc    420
catcaattaa gaaaaaaatt tagcttgtag ataaattcag aagttttatt attccaattg    480
agtgtaaagg cataactaca ggagggagtg tgcaaaatga tccgttactg cttaaccagt    540
tatagagagg atcttgttat cctggatata attaatgata gtttcagcat agtgcctgac    600
gcaggtagct tgctaaaaga aagagataaa ttgcttaaag aattcccaca actatcttac    660 tttttttgaca gtgaatatca tattggaagt gtttctcgta atagtgacac ttcttttctt    720
gaagaacgct ggtttctacc agaacctgac aaaacattat ataagtgttc tctatttaaa    780
cgatttatat tattactcaa agtctttttac tatagctgga atattgaaaa aaaagggatg    840
gcatggattt tcataagtaa taaaaaagag aataggctat actccttgaa tgaagagcat    900
cttatccgga aagaaattag taatctttcc attatctttc atcttaatat ttttaaatct    960
gactgtctta cctattcata cgcactaaaa agaattctta attccagaaa tattgatgct   1020
catcttgtta ttggtgtaag gacacaacct ttttatagcc actcttgggt ggaggttggg   1080
ggacaagtta tcaatgatgc tcccaatatg cgggataaat tatctgttat tgcagagata   1140
tagttatgga aatatttaat gtcaagttaa atgatacttc aattagaatt attttctgta   1200
aaacgctttc tgccttccgg acagaaaata ccatcgttat gctcaaagga aaagcagttt   1260
caaatggcaa acctgtatcc acagaggaga ttgccagagt agtggaagaa aaaggtgttt   1320
cagaagtaat agaaaattta gatggtgttt tctgtatcct aatttatcat tttaatgatc   1380

```
tccttatagg gaaaagcatt caatcaggcc ccgctctatt ttattgtaaa aagaatatgg    1440
atatttttgt ttcggataaa atttctgata tcaaatttt gaatccagat atgacattca     1500
gtctaaatat aaaaatggca gaacattatc tgtcaggaaa tcgaatagca acccaggaat    1560
cactaatcac tggcatttac aaagtaaata atggtgagtt tataaaattt aataatcagt   1620
tgaaacctgt gctacttcgt gatgagttta gtattaccaa aaagaacaat tcaactatcg   1680
acagtatcat tgataatatt gagatgatgc gggataatag aaaaatagcc ctattattct   1740
ccggaggatt ggattctgca ttaattttc acacacttaa agaatcaggt aacaaattct    1800
gcgcttatca ttttttttct gatgaatctg atgacagtga aaagtatttt gctaaggaat   1860
actgttcaaa atatggagtt gattttatat ctgttaataa aaacatcaac tttaatgaaa   1920
aactttattt caatttaaat cctaatagtc cggacgaaat ccctttgata tttgaacaga   1980
cagatgaaga aggtgaaggt cagccccca tagacgatga tttattatat ctatgtggtc    2040
acggtggaga tcatattttc ggacaaaatc cttcagaact ttttggcatt gatgcatatc   2100
gaagtcatgg cttgatgttt atgcataaaa aaatagtaga attttccaat ctcaagggaa   2160
agagatataa agatatcata ttttcaaata tttccgcatt cattaataca tccaacggat   2220
gttctccagc aaagcaagag cacgtatcag atatgaaact tgcctctgct cagtttttg    2280 caactgatta tacaggaaaa attaataaac taactccatt cctgcataaa aatattatcc   2340
agcattatgc tggcttacca gttttagtc tatttaacca gcactttgat cgttatcccg    2400
ttcgttatga agcgtttcaa cgatttggtt cagatatttt ctggaaaaaa accaaacggt   2460
catcttcaca gctaatattc agaattctat ccggtaaaaa ggatgaacta gtgaatacaa   2520
taaaacagtc aggattaatt gaaatattag gcattaacca tattgaatta gaaagcatt    2580 tgtatgaaaa tacgactaca cgtctgacaa cggaactacc atatatactt aacttatacc   2640
gtctggcaaa attcattcaa cttcaatcca ttgattataa aggttaatta tggaaagaaa   2700
acagaaaaac tcattattta attatattta ttcattaatg gatgcaagag gtaaattttt   2760
attcttttcc atgttattca ttacatcatt atcatcgata tcatatctat tttcaccatt    2820
gattcttgca aagattacag atttactgtc tggctcattg tcaaattta gttatgaata    2880 tctggttta cttgcctgtt tatacatgtt ttgcgttata tctaataaag caagtgtttt    2940
tttatttatg atactgcaaa gtagtctacg tattaacatg cagaaaaaa tgtcgctaaa    3000 atatttgaga gaattgtata acgaaaatat aactaacttg agtaaaaata atgctggata   3060
tacaacgcaa agtcttaacc aggcttcaaa tgacatttat attcttgtga gaatgtttc    3120 ccagaatatc ctgtcacctg ttatacaact tatttctact attgttgttg ttttatctac   3180
gaaggactgt ttttctgccg gtgtgttttt tctctatatt ctggtatttg taattttaa    3240 taccagactg actggcagtt tagcgtcact cagaaaacac agcatggata tcactcttaa   3300
ctcttatagt ctgttatctg atactgttga taacatgata gcagctaaaa agaataatgc   3360
attaagactt atttctgaac gttatgaaga tgctctcact caggaaaaca atgctcagaa   3420
aaaatactgg ttactcagtt ctaaagttct tttattgaac tctttacttg ctgtaatatt   3480
atttggttct gtattcatat ataatatttt aggtgtgctg aatggtgtag ttagtatcgg   3540
ccacttcatt atgattacat catatatcat tcttctttca acgccagtgg aaaatatagg   3600
ggcattgcta agtgagatca ggcagtcaat gtctagcctg gcaggtttta ttcaacgtca   3660
tgccgagaat aaagccacat ctccttcaat accttttctc aacatggagc gaaaattaaa   3720
```

```
cctgtccata agagagcttt catttagcta tagtgatgat aaaaaaatac ttaattcagt    3780
cagtcttgac cttttaccg gaaaaatgta ttcattaacc ggacccagtg gttcaggaaa    3840
atccacccct gtaaaaataa tatcaggtta ctataaaaat tactttggag acatttatct    3900
gaatgatata tccttacgta atatcagtga tgaggatttg aatgatgcta tttactacct    3960
aacacaagat gattatattt ttatggatac actacgattt aatctccggc tcgcaaatta    4020
cgacgcgtca gaaaatgaaa tgtttaaagt tcttaaactg gcaaatcttt ctgtcgtcaa    4080
caatgaacca gtgagtctgg atacacacct tataaacaga ggcaataact attcaggagg    4140
gcaaaaacaa cgaatttcgt tagcgcgact gtttttgaga aaacctgcaa taattattat    4200
tgatgaagcc acatcggctc tggattatat taatgaatca gaaattttat catcaataag    4260
aactcatttt cctgatgcgt taattataaa tattagtcac cgaataaatc ttctggagtg    4320
ttccgattgt gtttatgtat tgaatgaagg aaatattgtt gcttctggcc atttcaggga    4380
tttgatggtc agcaatgaat acatatcggg actggcttct gttactgaat aaaatatctg    4440
actcctgctc tgtattcaga aagggagtcg cttggaaaac ggaatttttc ccacg          4495
```

```
<210> SEQ ID NO 10
<211> LENGTH: 21
<212> TYPE: PRT
<213> ORGANISM: Artificial sequence
<220> FEATURE:
<223> OTHER INFORMATION: Primer

<400> SEQUENCE: 10

Gly Gly Ala Gly His Val Pro Glu Tyr Phe Val Gly Ile Gly Thr Pro
1               5                   10                  15

Ile Ser Phe Tyr Gly
            20
```

MICROCIN MCCY, AND PREPARATION METHOD AND USE THEREOF

CROSS-REFERENCE TO RELATED APPLICATIONS

This application claims the benefit of and priority from Chinese Patent Application No. 2021100879729, filed Jan. 22, 2021, the entire disclosures of which are incorporated herein by reference.

The material in the ASCII text file jiaq_11085_20210420_sequence_listing, filed with the present application via EFS-web, created on Apr. 20, 2021, having the size of 19 KB, is incorporated by reference in the specification for all purposes.

TECHNICAL FIELD

The present disclosure belongs to the field of biotechnology, and particularly relates to a Microcin MccY, and a preparation method and use thereof.

BACKGROUND

A Microcin (Mcc) is a class of micromolecule bacteriostatic peptides secreted by an intestinal bacterium, with a molecular weight of about 10 kDa. The Microcin is encoded by a plasmid-related or chromosome-related gene cluster of the bacterium. In this gene cluster, some genes are relatively conserved, and at least 4 genes are involved in encoding the Microcin, including precursor gene, post-transcriptional modification gene, secretory gene, and autoimmune gene. In this gene cluster, structural gene mainly encodes the precursor of the Microcin which is the main structural constituent of the Microcin; the modification gene can process the precursor of the Microcin, make it easier to be recognized by a corresponding receptor, and meanwhile give better play to the biological activity of the Microcin; the secretory gene encodes a secretion-related protein; and the immune gene can protect a bacterium from being poisoned by the Microcin secreted by itself. The Microcin is mainly divided into two types: type I and type II. The Microcin type I is encoded by a plasmid, while the Microcin type II is encoded by a chromosome.

At present, 15 kinds of Microcins have been found, and they have certain differences in the bacteriostatic mechanism. The main limitation on the Microcin MccJ25 which has been studied more, is its relatively narrower bacteriostatic spectrum, and it only exerts bacteriostatic and bactericidal effects on closely-related strains of intestinal flora. For example, MccJ25 has a better bactericidal effect on *Salmonella entertidis* than on *Escherichia coli*., and it has no bactericidal effect on other common serotypes of enteritis subfamily such as mouse typhus and *pullorum* diseases due to the reason that MccJ25 acts on the iron carrier receptor FhuA of *Salmonella*, while the expression of the receptor FhuA in *Salmonella Pullorum* is terminated in advance. Therefore, for common opportunistic pathogens such as *Salmonella Pullorum, Salmonella typhimurium, Salmonella kentucky, Salmonella Infantis, Salmonella London, Shigella sonnei*, etc., only using MccJ25 for bacteriostasis is obviously not broad-spectrum.

SUMMARY

In order to overcome the shortcoming of relatively narrower bacteriostatic spectrum of the existing Microcin, an objective of a first aspect of the present disclosure is to provide a Microcin MccY.

An objective of a second aspect of the present disclosure is to provide a polynucleotide for encoding the Microcin MccY.

An objective of a third aspect of the present disclosure is to provide a plasmid.

An objective of a fourth aspect of the present disclosure is to provide an engineered strain.

An objective of a fifth aspect of the present disclosure is to provide a method for preparing the Microcin MccY.

An objective of a sixth aspect of the present disclosure is to provide use of the aforementioned Microcin MccY and/or engineered strain in a bacteriostatic agent and/or a feed.

An objective of a seventh aspect of the present disclosure is to provide a formulation.

In order to achieve the aforementioned objective, the technical solution adopted by the present disclosure is as follows.

In a first aspect of the present disclosure, provided is a Microcin MccY, wherein the amino acid sequence of the Microcin MccY is:

a) GGRGHIAEYFSGPITQVSFYG (SEQ ID NO.1); or b) an amino acid sequence which is obtained by modifying the amino acid sequence as shown in SEQ ID NO.1 by substitution, deletion or addition of one or more amino acid residues, and has a function of the Microcin MccY.

In a second aspect of the present disclosure, provided is a polynucleotide, wherein the polynucleotide comprises a polynucleotide encoding the Microcin MccY of the first aspect.

Preferably, the polynucleotide comprises mcyA (SEQ ID NO.2), mcyB (SEQ ID NO.3), mcyC (SEQ ID NO.4), and mcyD (SEQ ID NO.5).

Further, the sequence of the polynucleotide is as shown in SEQ ID NO.6.

In a third aspect of the present disclosure, provided is a plasmid comprising the polynucleotide of the second aspect.

Preferably, the plasmid further comprises a vector.

Preferably, the vector is pET-28a (+).

In a fourth aspect of the present disclosure, provided is an engineered strain comprising the plasmid of the third aspect.

Preferably, the engineered strain is *Escherichia coli*. BL21 (DE3) comprising the plasmid of the third aspect.

In a fifth aspect of the present disclosure, provided is a method for preparing a Microcin MccY, wherein the Microcin MccY is prepared by conducting fermentation with the engineered strain of the fourth aspect.

Preferably, in the method for preparing the Microcin MccY, the engineered strain of the fourth aspect is inoculated into a fermentation medium, and subjected to fermentation at 100-300 r/min and 32-40° C. for 11-18 hours.

Preferably, the fermentation medium is at least one of LB medium, M9 basic salt medium, and M20 basic salt medium.

Preferably, the fermentation medium further comprises kanamycin and isopropyl-β-D-thiogalactoside.

In a sixth aspect of the present disclosure, provided is use of the Microcin MccY of the first aspect and/or the engineered strain of the fourth aspect in a bacteriostatic agent and/or a feed.

Preferably, an object on which the bacteriostatic agent acts comprises *Salmonella Pullorum, Salmonella typhimurium, Salmonella kentucky, Salmonella Infantis, Salmonella London*, and *Shigella sonnei*.

In a seventh aspect of the present disclosure, provided is a formulation comprising the Microcin MccY of the first aspect and/or the engineered strain of the fourth aspect.

Preferably, the formulation is a bacteriostatic agent and/or a feed.

Preferably, the object on which the bacteriostatic agent acts at least comprises *Salmonella Pullorum, Salmonella typhimurium, Salmonella kentucky, Salmonella Infantis, Salmonella* London, and *Shigella sonnei*.

Preferably, the formulation further comprises a Microcin MccJ25.

The beneficial effects of the present disclosure are as follows.

The present disclosure provides a Microcin MccY for the first time. Compared with the Microcin MccJ25 that only has a bactericidal activity against a small part of serotypes of *Salmonella* such as *Salmonella enteritidis*, the Microcin MccY has bacteriostatic/bactericidal effects on *Salmonella Pullorum, Salmonella typhimurium, Salmonella kentucky, Salmonella Infantis, Salmonella London*, and *Shigella sonnei*, and can kill other serotypes of *Salmonella* that MccJ25 cannot kill. Especially, The Microcin MccY has an outstanding bactericidal effect on *Salmonella typhimurium* and *Salmonella Pullorum* which are common in livestock and poultry production, and meanwhile it also has bacteriostatic/bactericidal effects on *Shigella sonnei*. Therefore, The Microcin MccY of the present application overcomes the shortcoming of the narrow spectrum of the Microcin, has breakthrough significance, and has the potential as a substitute to antibiotics.

The method for preparing the Microcin MccY as provided by the present disclosure has the advantages of simple operation and low cost, and can realize large-scale production.

The formulation comprising MccY and MccJ25 as provided by the present disclosure can effectively inhibit intestinal flora represented by *Salmonella typhimurium, Salmonella enteritidis, Salmonella Pullorum, Salmonella kentucky, Salmonella Infantis* and *Salmonella London*, and maintain the stability of intestinal microecology of a targeted host.

DETAILED DESCRIPTION

The present disclosure will be further explained in detail hereafter by specific examples.

Unless otherwise specified, the materials and reagents used in this example are commercially available reagents and materials.

The information of the instruments used in this example is shown in Table 1.

TABLE 1

| Information of used instrument | |
|---|---|
| Instrument Name | Company |
| ZHJH-C1214C super clean bench | Suzhou Purification Equipment Co. Ltd. |
| DK-8D Electro-Thermostatic Constant-Temperature Water Bath | Shanghai Bluepard Instruments Co., Ltd. |
| GDS8000PC gel imaging and analysis system | UVP |
| ND-1000 spectrophotometer | NanoDrop |
| T3000 Thermocycler PCR amplifier | Whatman Biometra |
| Micro-adjustable pipette | Eppendorf, Germany |
| Power PacTM basic electrophoresis meter | BIO-RAD |
| Centrifuge | Eppendorf, Germany |

Example 1 Construction and Expression of MccY Plasmid

Figure 4:
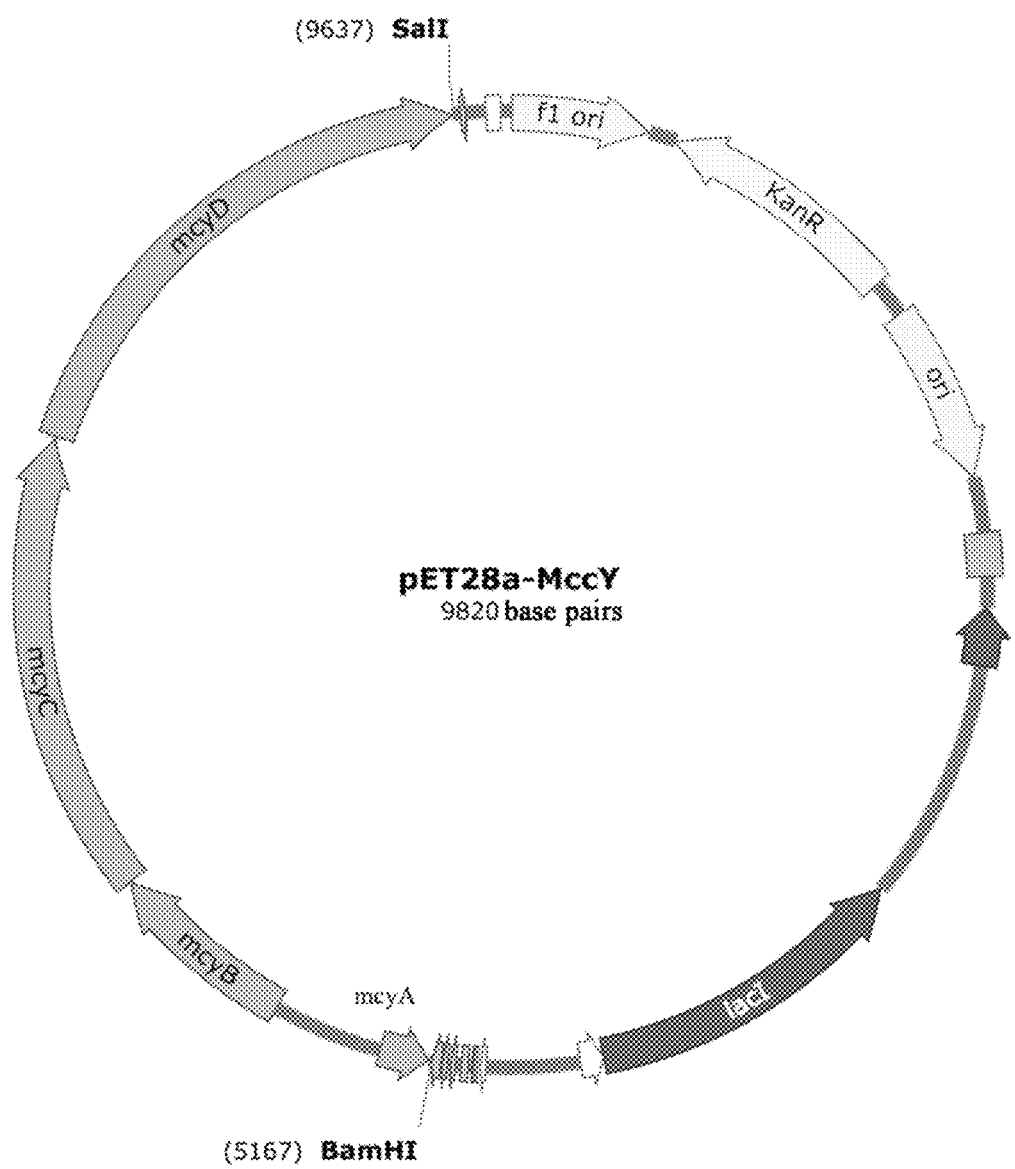
FIG. 4 is a diagram showing a pET-28a(+)-MccY plasmid constructed in Example 1.

A mccy gene fragment (Guangzhou IGE Biotechnology OGY Ltd) was synthesized. The mccy gene had a total length of 4,458 bp, and its sequence was as shown in SEQ ID NO.6, which comprised all four target genes, including mcyA (SEQ ID NO.2), mcyB (SEQ ID NO.3), mcyC (SEQ ID NO.4) and mcyD (SEQ ID NO.5) (by Blast search of mcyA, mcyB, mcyC and mcyD genes respectively, it was found that the amino acid sequence homologies of them with mcjA, mcjB, mcjC and mcjD genes of *Escherichia coli*. MccJ25 were 51.9%, 54.8%, 52.3% and 70.4%, respectively. The homology of this sequence with MccJ25 is not high, but it has all the basic structural genes of Microcin type I.) The mccy gene fragment was subjected to double enzyme digestion by restriction endonucleases (SalI, BamHI) available from NEB (the enzyme digestion reaction system was shown in Table 2), and then recovered and purified from gel, to obtain a mccy having open cohesive termini. Meanwhile, a vector pET-28a(+) was subjected to double enzyme digestion by the restriction endonucleases (SalI, BamHI) (the enzyme digestion reaction system was shown in Table 2), and then recovered and purified from gel by using a DNA gel recovery kit available from OMEGA to obtain a linearized vector having open cohesive termini. The linearized vector pET-28a(+) was ligated with the mccy having open cohesive termini through a T4 DNA ligase (the ligation system was shown in Table 3, and the reaction condition was: reacting at 16° C. for 3 h). The ligation product was transformed into an *Escherichia coli*. DH5a strain, and screened for positive monoclones by utilizing the kanamycin resistance of the plasmid. The monoclonal colonies were picked, subjected to PCR amplification by using universal primers T7-F (TAATACGACTCACTATAGGG, SEQ ID NO.7)/T7-R (GCTAGTTATTGCTCAGCGG, SEQ ID NO.8) for a pET-28a(+) plasmid multicloning site region, and the plasmids were extracted for sequencing verification. The target band was about 4,700 bp, and the sequencing was errorless. Successfully-cloned pET-28a(+)-MccY plasmids were obtained (a diagram showing plasmid was shown in FIG. 4). The pET-28a(+)-MccY plasmid was introduced into a BL21 (DE3) competent cell by a heat shock chemical transformation method, and the specific process was as follows: mixing the pET-28a(+)-MccY plasmid with the BL21(DE3) competent cell uniformly, putting in a water bath kettle at 42° C. for incubation for 90 s, then quickly transferring onto ice for incubation for 2 min, then adding with 300 μL of SOC medium, culturing at 37° C. and 200 r/min for 1 h, and then spreading onto a plate containing kanamycin (50 μg/mL), and inverting in a bacterial incubator for culturing overnight. On the next day, the positive monoclonal colonies were picked into and cultured in LB medium containing kanamycin resistance (50 μg/mL), and then subjected to PCR amplification identification by using universal primers T7-F (TAATACGACTCACTATAGGG, SEQ ID No.7)/T7-R (GCTAGTTATTGCTCAGCGG, SEQ ID NO.8) for the multcloning site region. The target band was about 4,700 bp, and the diagram showing the plasmid pET-28a(+)-MccY could be seen in FIG. 4.

TABLE 2

Enzyme digestion reaction system

| Reagent | Volume (μL) |
|---|---|
| FD buffer | 5 |
| Endonuclease SalI/BgIII | 2.5 |
| Endonuclease BamHI/HindIII | 2.5 |
| mccy gene fragment/mccj25 gene fragment (vector) | 10 |
| ultrapure water | 30 |
| In total | 50 |

TABLE 3

Ligation reaction system

| Reagent | Volume (μL) |
|---|---|
| Reaction buffer | 1 |
| inserted fragment | 1.5 |
| linear plasmid | 4 |
| T4 DNA ligase | 0.5 |
| ultrapure water | 3 |
| In total | 10 |

The pET-28a(+)-MccY-containing BL21(DE3) bacteria were resuscitated in a LB plate with a kanamycin concentration of 30 μg/mL, and cultured to grow fresh bacterial lawns. A loop of the bacteria was taken and inoculated into a 250 ml Erlenmeyer flask containing 100 mL nutrient broth (the M9 medium), and then kanamycin, isopropyl-β-D-thiogalactoside (IPTG) (with the final concentration of kanamycin being 30 μg/mL and the final concentration of IPTG being 0.1M) were added into the Erlenmeyer flask. The Erlenmeyer flask was placed and cultured in a shaker (with the culture conditions being: 200 r/min, 37° C. and 14 h). The bacteria solution after the expression was collected, and centrifuged at 5,000 r/min for 20 min, and then the supernatant after the centrifugation was collected and filtered with a 0.22 μm filter membrane to obtain the Microcin MccY. Since the Microcin had a stable structure, could resist high temperature and could be frozen and thawed repeatedly, it was cryopreserved in a refrigerator at −20° C. for later use.

Example 2 Construction and Expression of Engineered Strain Containing an Empty Plasmid A vector pET-28a(+) was introduced into a BL21(DE3) competent cell (the method was the same as that of Example 1) to obtain pET-28a(+)-containing BL21(DE3) bacteria. The pET-28a(+)-containing BL21(DE3) bacteria were resuscitated in a LB plate with a kanamycin concentration of 30 μg/mL, and cultured to grow fresh bacterial lawns. A loop of the bacteria was taken and inoculated into a 250 ml Erlenmeyer flask containing 100 mL of M9 basic salt medium, and then kanamycin, isopropyl-β-D-thiogalactoside (IPTG) (with the final concentration of kanamycin being 30 μg/mL and the final concentration of IPTG being 0.1M) were added into the Erlenmeyer flask. The Erlenmeyer flask was placed and cultured in a shaker (with the culture conditions being: 200 r/min, 37° C. and 14 h). The bacteria solution after the expression was collected, and centrifuged at 5,000 r/min for 20 min, and then the supernatant after the centrifugation was collected and filtered with a 0.22 μm filter membrane to obtain the filtrate.

Example 3 Construction and Expression of MccJ25 Plasmid

Figure 5:
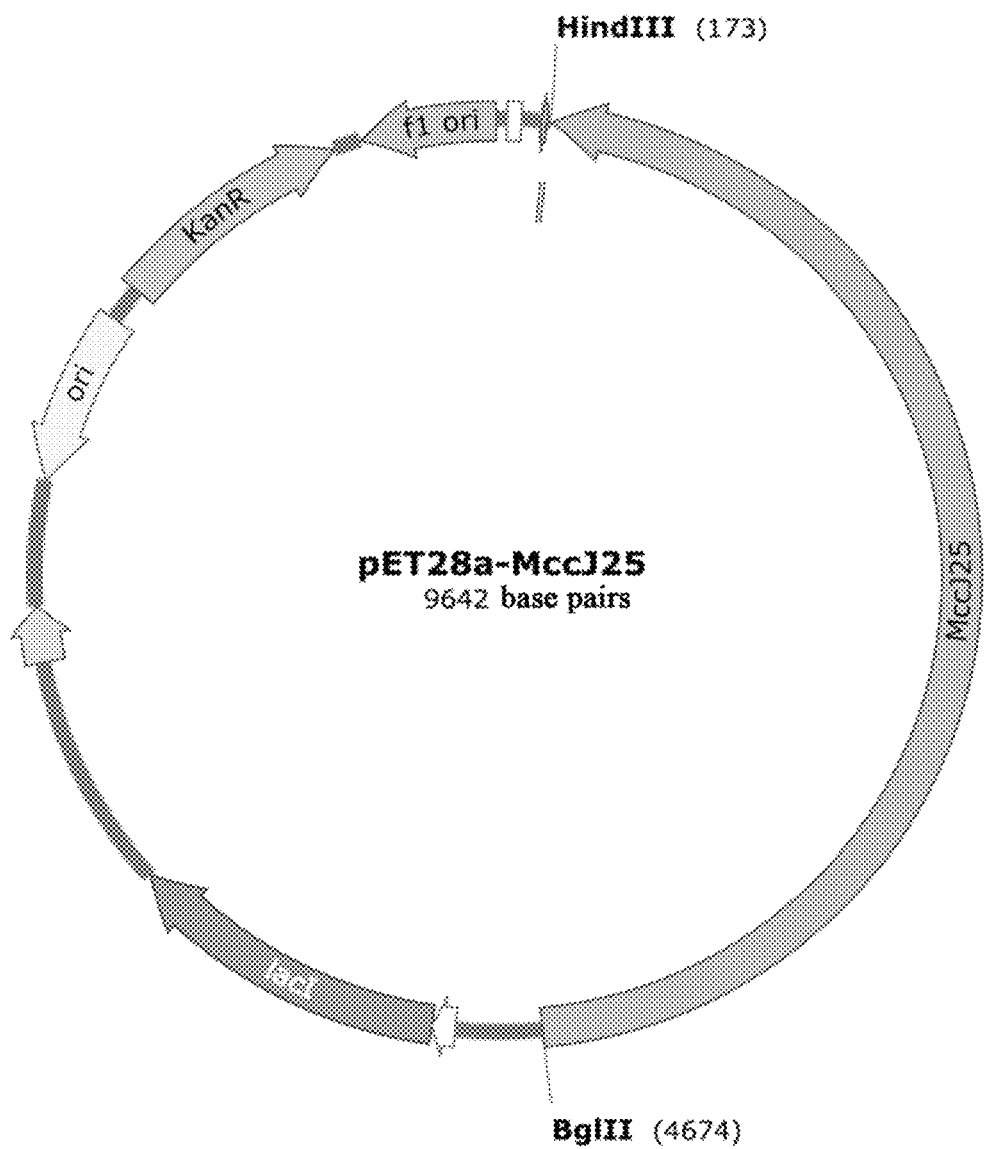
FIG. 5 is a diagram showing a pET-28a(+)-MccJ25 plasmid constructed in Example 3.

A mccj25 gene fragment (Guangzhou IGE Biotechnology OGY Ltd) was synthesized. The mccj25 gene had a total length of 4,495 bp, and its sequence was as shown in SEQ ID NO.9. The mccj25 gene fragment was subjected to double enzyme digestion by restriction endonucleases (BgIII, HindIII) available from NEB (the enzyme digestion reaction system was shown in Table 2), and recovered and purified from gel, to obtain a mccj25 having open cohesive termini. Meanwhile, a vector pET-28a(+) was subjected to double enzyme digestion by the restriction endonucleases (BgIII, HindIII) (the enzyme digestion reaction system was shown in Table 2), and then recovered and purified from gel by using a DNA gel recovery kit available from OMEGA to obtain a linearized vector having open cohesive termini. The linearized vector pET-28a(+) was ligated with the mccj25 having open cohesive termini through a T4 DNA ligase (the ligation system was shown in Table 3, and the reaction condition was: reacting at 16° C. for 3 h). The ligation product was transformed into an *Escherichia coli*. DH5a strain, and screened for positive monoclones by utilizing the kanamycin resistance of the plasmid. The monoclonal colonies were picked, subjected to PCR amplification by using universal primers T7-F (TAATACGACTCACTATAGGG, SEQ ID NO.7)/T7-R (GCTAGTTATTGCTCAGCGG, SEQ ID NO.8) for a pET-28a(+) plasmid multicloning site region, and the plasmids were extracted for sequencing verification. The target band was about 4,500 bp, and the sequencing was errorless. Successfully-cloned pET-28a(+)-McJ25 plasmids were obtained (a diagram showing the plasmid was shown in FIG. 5). The pET-28a(+)-McJ25 plasmid was introduced into a BL21(DE3) competent cell by a heat shock chemical transformation method, and the specific process was as follows: mixing the pET-28a(+)-McJ25 plasmid with the BL21(DE3) competent cell uniformly, putting in a water bath kettle at 42° C. for incubation for 90 s, then quickly transferring onto ice for incubation for 2 min, then adding with 300 µL of SOC medium, culturing at 37° C. and 200 r/min for 1 h, and then spreading onto a plate containing kanamycin (50 µg/mL), and inverting in a bacterial incubator for culturing overnight. On the next day, the positive monoclonal colonies were picked into and cultured in LB medium containing kanamycin resistance (50 µg/mL), and then subjected to PCR amplification identification by using universal primers T7-F (TAATACGACTCACTATAGGG, SEQ ID No.7)/T7-R (GCTAGTTATTGCTCAGCGG, SEQ ID NO.8) for the multicloning site region. The target band was about 4,700 bp, and the diagram showing the plasmid pET-28a(+)-McJ25 could be seen in FIG. 5.

The pET-28a(+)-McJ25-containing BL21(DE3) bacteria were resuscitated in a LB plate with a kanamycin concentration of 30 µg/mL, and cultured to grow fresh bacterial lawns. A loop of the bacteria was taken and inoculated into a 250 ml Erlenmeyer flask containing 100 mL nutrient broth (the M9 medium), and then kanamycin, isopropyl-β-D-thiogalactoside (IPTG) (with the final concentration of kanamycin being 30 µg/mL and the final concentration of IPTG being 0.1M) were added into the Erlenmeyer flask. The Erlenmeyer flask was placed and cultured in a shaker (with the culture conditions being: 200 r/min, 37° C. and 14 h). The bacteria solution after expression was collected, and centrifuged at 5,000 r/min for 20 min, and then the supernatant after centrifugation was collected and filtered with a 0.22 µm filter membrane to obtain the Microcin McJ25 (SEQ ID NO.10). Since the Microcin McJ25 had a stable structure, could resist high temperature and could be frozen and thawed repeatedly, it was cryopreserved in a refrigerator at −20° C. for later use.

Example 4 Test of Bacteriostatic Activities of McY and McJ25

1. Bacteriostatic effects of McY, McJ25 and the composition of McY and McJ25 against different serotypes of *Salmonella*

Figure 1:
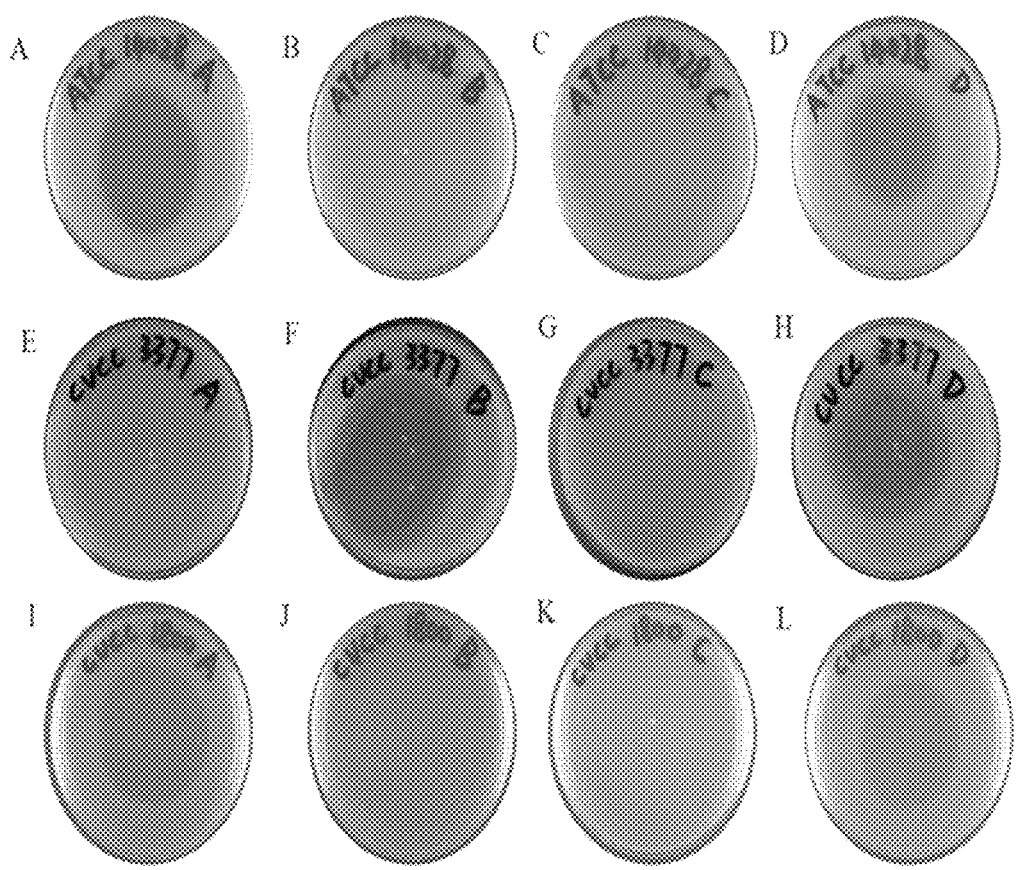
FIG. 1 is a diagram showing the bacteriostatic effects of the composition of MccY and MccJ25 in Example 4 against *Salmonella typhimurium, Salmonella Pullorum* and *Salmonella enteritidis*, wherein A, E and I are respectively panels showing the bacteriostatic effects of the filtrate (the Microcin MccY) expressed by pET-28a(+)-MccY-containing BL21(DE3) bacteria obtained in Example 1 against *Salmonella typhimurium, Salmonella enteritidis* and *Salmonella Pullorum*; B, F, and J are respectively panels showing the bacteriostatic effects of the filtrate (the Microcin MccJ25) expressed by pET-28a(+)-MccJ25-containing BL21(DE3) bacteria obtained in Example 3 against *Salmonella typhimurium, Salmonella enteritidis* and *Salmonella Pullorum*; C, G, and K are respectively panels showing the bacteriostatic effects of the filtrate expressed by pET-28a(+)-containing BL21(DE3) bacteria obtained in Example 2 against *Salmonella typhimurium, Salmonella enteritidis* and *Salmonella Pullorum*; and D, H, and L are respectively panels showing the bacteriostatic effects of the composition of MccY and MccJ25 against *Salmonella typhimurium, Salmonella enteritidis* and *Salmonella Pullorum*.

*Salmonella Pullorum* (strain name: CVCC1800), *Salmonella enteritidis* (strain name: CVCC3377) and *Salmonella typhimurium* (strain name: ATCC14028) were respectively resuscitated in a LB agar plate (with the formula as shown in Table 4) (cultured in a 5% $CO_2$ incubator at 37° C. for 16 h). Single colonies were picked and subjected to shaking culture until OD600=0.8. The bacterial solution was inoculated into a soft agar medium containing 5% LB (with the formula as shown in Table 5) at about 42° C. in a proportion of 1:1,000, and then spread onto a LB agar plate to form an upper and lower double-layer agar medium. 30 min later, after the soft agar was cooled and solidified, a mixed solution of 50 µL of the filtrate obtained in Example 1 (the Microcin McY), 50 µL of the filtrate obtained in Example 2, 50 µL of the filtrate obtained in Example 3 (the Microcin McJ25), 25 uL of the filtrate obtained in Example 1 (the Microcin McY) and 25 uL of the filtrate obtained in Example 3 (the Microcin McJ25) was taken and added into the upper and lower double-layer agar medium containing *Salmonella Pullorum*, *Salmonella enteritidis* and *Salmonella typhimurium*. The upper and lower double-layer agar medium was then placed into a 5% $CO_2$ bacterial incubator at 37° C. for static culture for 18 h, and then observed for a bacteriostatic ring. The results were shown in FIG. 1: the Microcin McY had inhibitory effects on *Salmonella Pullorum* and *Salmonella typhimurium*, the Microcin McJ25 had an inhibitory effect on *Salmonella* enteritis, and the combined use of McY and McJ25 had inhibitory effects on *Salmonella Pullorum*, *Salmonella enteritidis* and *Salmonella typhimurium*.

TABLE 4

Formula of LB agar medium

| Reagent | Reagent concentration |
| --- | --- |
| Agar | 15 |
| NaCl | 5 |
| Yeast powder | 10 |
| Tripton | 5 |
| In total | 35 |

TABLE 5

Formula of soft agar medium containing 5% LB

| Reagent | Reagent concentration |
| --- | --- |
| Agar | 5 |
| NaCl | 5 |
| Yeast powder | 5 |
| Tripton | 10 |
| In total | 25 |

2. Bacteriostatic effects of McY, McJ25 and the composition of McY and McJ25 against different serotypes of *Salmonella*

Figure 2:
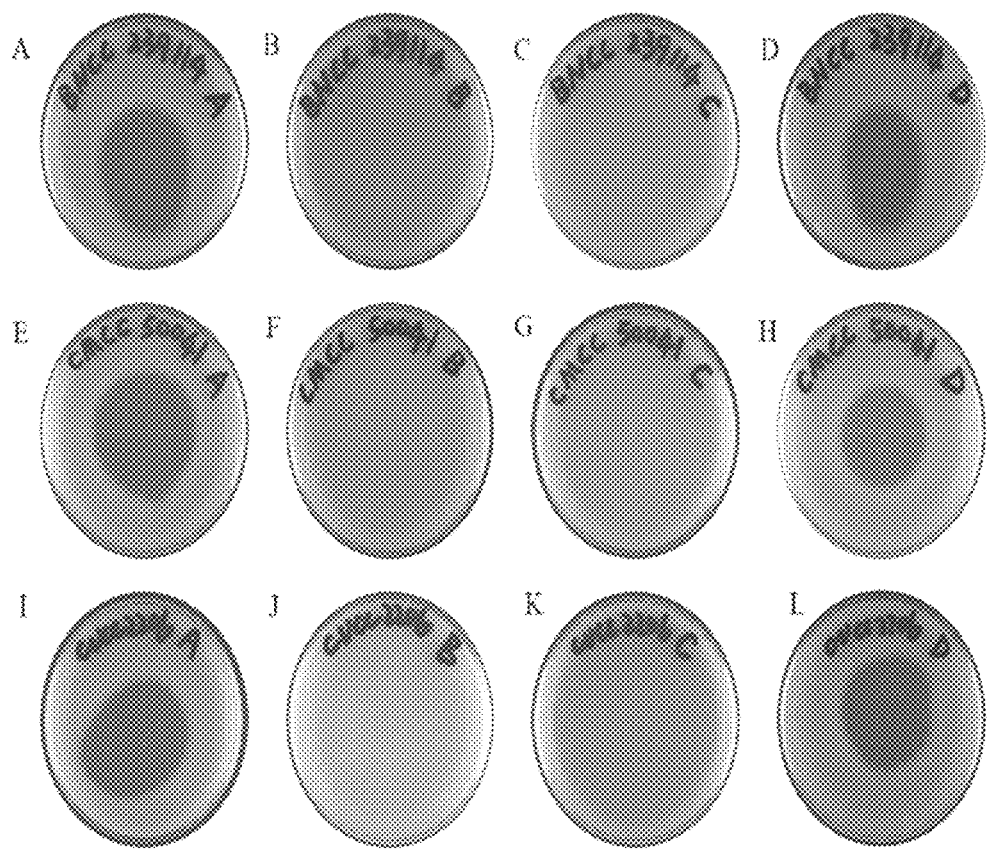
FIG. 2 is a diagram showing the bacteriostatic effects of the composition of MccY and MccJ25 in Example 4 against *Salmonella kentucky, Salmonella Infantis* and *Salmonella london*, wherein A, E and I are respectively panels showing the bacteriostatic effects of the filtrate (the Microcin MccY) expressed by pET-28a(+)-MccY-containing BL21(DE3) bacteria obtained in Example 1 against *Salmonella kentucky, Salmonella Infantis* and *Salmonella london*; B, F, and J are respectively panels showing the bacteriostatic effects of the filtrate (the Microcin MccJ25) expressed by pET-28a(+)-MccJ25-containing BL21(DE3) bacteria obtained in Example 3 against *Salmonella kentucky, Salmonella Infantis* and *Salmonella london*; C, G, and K are respectively panels showing the bacteriostatic effects of the filtrate expressed by pET-28a(+)-containing BL21(DE3) bacteria obtained in Example 2 against *Salmonella kentucky, Salmonella Infantis* and *Salmonella london*; and D, H, and L are respectively panels showing the bacteriostatic effects of the composition of MccY and MccJ25 against *Salmonella kentucky, Salmonella Infantis* and *Salmonella london*.

*Salmonella kentucky* (strain name: BNCC239114), *Salmonella Infantis* (strain name: CMCC50041) and *Salmonella london* (strain name: CVCC2206) were respectively resuscitated in a LB agar plate (with the formula as shown in Table 4) (cultured in a 5% $CO_2$ incubator at 37° C. for 16 h). Single colonies were picked and subjected to shaking culture until OD600=0.8. The bacterial solution was inoculated into a soft agar medium containing 5% LB (with the formula as shown in Table 5) at about 42° C. in a proportion of 1:1,000, and then spread onto a LB agar plate to form an upper and lower double-layer agar medium. 30 min later, after the soft agar was cooled and solidified, a mixed solution of 50 μL of the filtrate obtained in Example 1 (the Microcin MccY), 50 μL of the filtrate obtained in Example 2, 50 μL of the filtrate obtained in Example 3 (the Microcin MccJ25), 25 uL of the filtrate obtained in Example 1 (the Microcin MccY) and 25 uL of the filtrate obtained in Example 3 (the Microcin MccJ25) was taken and added into the upper and lower double-layer agar medium containing *Salmonella Pullorum*, *Salmonella enteritidis* and *Salmonella typhimurium*. The upper and lower double-layer agar medium was then placed into a 5% $CO_2$ bacterial incubator at 37° C. for static culture for 18 h, and then observed for a bacteriostatic ring. The results were shown in FIG. 2: the Microcin MccY had inhibitory effects on all of *Salmonella kentucky*, *Salmonella Infantis* and *Salmonella london*, the Microcin MccJ25 had no inhibitory effect on all of *Salmonella kentucky*, *Salmonella Infantis* and *Salmonella london*, and the combined use of MccY and MccJ25 had efficient inhibitory effects on *Salmonella* kentucky, *Salmonella Infantis* and *Salmonella london*.

3. Bacteriostatic Effect of MccY Against *Shigella*

Figure 3:
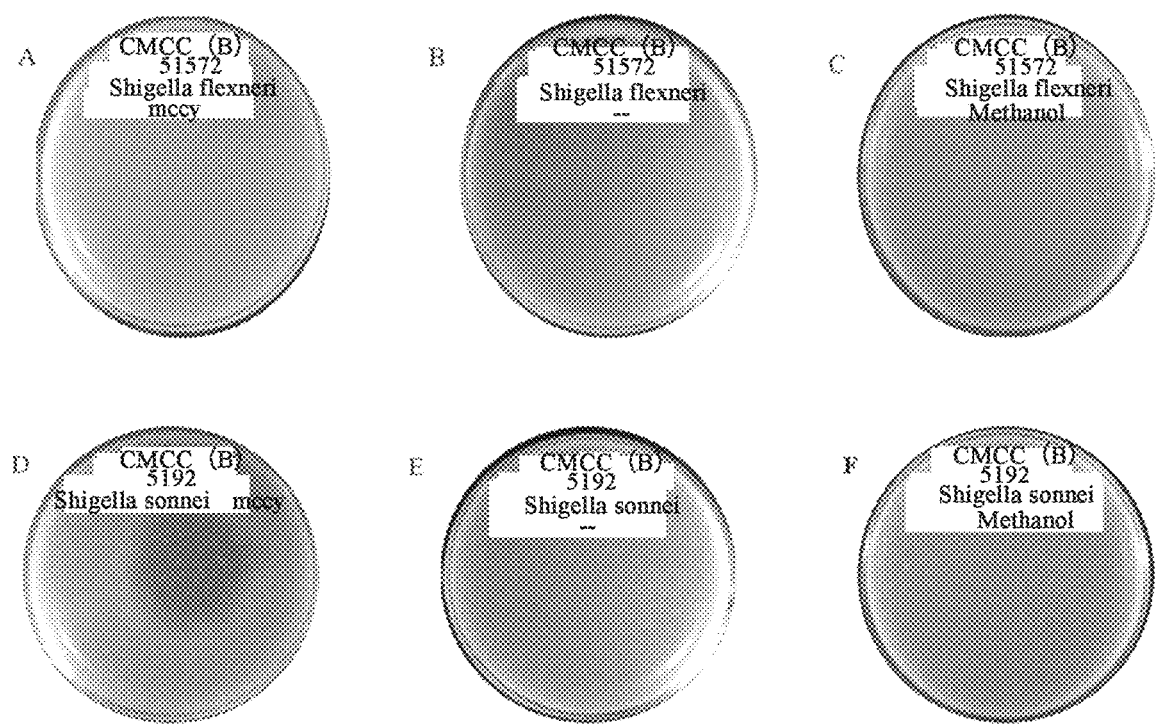
FIG. 3 is a diagram showing the bacteriostatic effect of the Microcin MccY in Example 4 against *Shigella*, wherein A is a panel showing the bacteriostatic effect of the filtrate (the Microcin MccY) expressed by pET-28a(+)-MccY-containing BL21(DE3) bacteria obtained in Example 1 against *Shigella flexneri*; B is a panel showing the bacteriostatic effect of the filtrate expressed by pET-28a(+)-containing BL21(DE3) bacteria obtained in Example 2 against *Shigella flexneri*; C is a panel showing the bacteriostatic effect of methanol against *Shigella flexneri*; D is a panel showing the bacteriostatic effect of a filtrate (the Microcin MccY) expressed by pET-28a(+)-MccY-containing BL21(DE3) bacteria obtained in Example 1 against *Shigella sonnei*; E is a panel showing the bacteriostatic effect of the filtrate expressed by pET-28a(+)-containing BL21(DE3) bacteria obtained in Example 2 against *Shigella sonnei*; and F is a panel showing the bacteriostatic effect of methanol against *Shigella sonnei*.

*Shigella flexneri* (strain name: CMCC51572) and *Shigella sonnei* (strain name: CMCC51592) were respectively resuscitated in a LB agar plate (with the formula as shown in Table 4) (cultured in a 5% $CO_2$ incubator at 37° C. for 16 h). Single colonies were picked and subjected to shaking culture until $OD_{600}$=0.8. The bacterial solution was inoculated into a soft agar medium containing 5% LB (with the formula as shown in Table 5) at about 42° C. in a proportion of 1:1,000, and then spread onto a LB agar plate to form an upper and lower double-layer agar medium. 30 min later, after the soft agar was cooled and solidified, each 50 μL of the filtrate obtained in Example 1 (the Microcin MccY) and methanol were respectively taken and added into the upper and lower double-layer agar medium containing *Shigella flexneri* and *Shigella sonnei* (the control group was added with the same amount of the filtrate obtained in Example 2). The upper and lower double-layer agar medium was then placed into a 5% $CO_2$ bacterial incubator at 37° C. for static culture for 18 h, and then observed for a bacteriostatic ring. The results were shown in FIG. 3: *Shigella flexneri* was not sensitive to MccY, while *Shigella sonnei* was sensitive to MccY, namely, MccY had a bacteriostatic effect on *Shigella sonnei*.

The above examples are preferred examples of the present disclosure. However, the implementation of the present disclosure is not limited by the above examples. Any other change, modification, substitution, combination, and simplification made without departing from the spiritual essence and principle of the present disclosure should be an equivalent replacement manner, and all are included in a claimed scope of the present disclosure.

What is claimed is:

1. A polynucleotide encoding the Microcin MccY, wherein the amino acid sequence of the Microcin MccY is: GGRGHIAEYFSGPITQVSFYG (SEQ ID NO:1); and
    wherein the sequence of the polynucleotide comprises mcyA (SEQ ID NO:2), mcyB (SEQ ID NO:3), mcyC (SEQ ID NO:4), and mcyD (SEQ ID NO:5).

2. A plasmid, comprising the polynucleotide according to claim 1.

3. An engineered strain comprising the plasmid according to claim 2.

4. A method for preparing a Microcin MccY, wherein the Microcin MccY is prepared by conducting fermentation with the engineered strain according to claim 3.

5. The preparation method according to claim 4, wherein the engineered strain according to claim 3 is inoculated in a fermentation medium, and subjected to fermentation at 100-300 r/min and 32-40° C. for 11-18 h.

6. A formulation comprising: the engineered strain according to claim 3.

7. A formulation, comprising the polynucleotide according to claim 1.

* * * * *